United States Patent [19]

Wolf et al.

[11] Patent Number: 5,126,441
[45] Date of Patent: Jun. 30, 1992

[54] BISGLYCOSIDES

[75] Inventors: Gerhard Wolf, Mannheim; Richard R. Schmidt; Karin Jankowski, both of Constance; Andreas Terjung, Radolfzell, all of Fed. Rep. of Germany

[73] Assignee: BASF Aktiengesellschaft, Ludwigshafen, Fed. Rep. of Germany

[21] Appl. No.: 655,776

[22] Filed: Feb. 15, 1991

[30] Foreign Application Priority Data

Feb. 16, 1990 [DE] Fed. Rep. of Germany ....... 4004884

[51] Int. Cl.$^5$ .............................. A61K 31/70
[52] U.S. Cl. ...................... 536/18.1; 536/4.1; 536/1.1; 536/120; 521/115; 521/122; 521/129
[58] Field of Search ........... 536/4.1, 18.6, 1.1; 528/272; 514/24; 521/115, 122, 129

[56] References Cited

U.S. PATENT DOCUMENTS

| | | | |
|---|---|---|---|
| 4,043,951 | 8/1977 | Prokai et al. | 521/111 |
| 4,103,006 | 7/1978 | Sih | 536/18.1 |
| 4,931,483 | 6/1990 | Matsuoka et al. | 521/137 |
| 4,963,399 | 10/1990 | Gill | 521/115 |

FOREIGN PATENT DOCUMENTS

| | | |
|---|---|---|
| 0096292 | 12/1983 | European Pat. Off. . |
| 0133739 | 3/1985 | European Pat. Off. . |
| 0306651 | 3/1989 | European Pat. Off. . |
| 8601512 | 3/1986 | World Int. Prop. O. . |

OTHER PUBLICATIONS

Wuelknitz, et al; Chem Abstracts; 111 (116) 140524; 1989.
Tenside Surfactants Detergents, Band 26, Sep./Oct. 1989, Munchen Th. Bocker. J. Thiem "Synthese und Eigenschaften von Kohlenhydraftensiden".
Seiten 318-324 *Seiten 322,323*.
Angewandte Chemie, Band 98, 1986, Weinheim R. R. Schmidt "Neue Methoden zur Glycosid- und Oligo-sachharidsynthese-gibt es Alternativen zur Koenigs-Knorr-Methode? Seiten" 213-236.

*Primary Examiner*—Ronald W. Griffin
*Assistant Examiner*—Louise Leary
*Attorney, Agent, or Firm*—Oblon, Spivak, McClelland, Maier & Neustadt

[57] ABSTRACT

Bisglycosides I $$\text{Gly}-\text{O}-\text{CHR}^2-(\text{CH}_2)_p-(\text{XR}^1)_n-(\text{CH}_2)_q-(\text{CHR}^3)_m-\text{O}-\text{Gly} \qquad \text{I}$$

where
X is C—R$^4$ or N,
R$^1$ is C$_1$-C$_{30}$-alkyl, C$_2$-C$_{30}$-alkenyl, O—C$_1$-C$_{30}$-alkyl or O—C$_2$-C$_{30}$-alkenyl when X is C—R$^4$, and is CO—C$_1$-C$_{30}$-alkyl or CO—C$_2$-C$_{30}$-alkenyl when X is N,
R$^2$ to R$^4$ are each hydrogen, C$_1$-C$_{30}$-alkyl or C$_2$-C$_{30}$-alkenyl,
n is from 1 to 3,
m is 0 or 1,
p and q are each from 0 to 2 and
Gly is a mono- or disaccharide composed of aldopentoses, aldohexoses and/or ketohexoses,
are used as surfactants or emulsifiers in detergents, cleaning agents and toiletries.

4 Claims, No Drawings

BISGLYCOSIDES

The present invention relates to novel bisglycosides of the general formula I $$\text{Gly—O—CHR}^2\text{—(CH}_2)_p\text{—(XR}^1)_n\text{—(CH}_2)_q\text{—(CHR}^3)_m\text{—O—Gly} \quad \text{I}$$

where

X is C—R$^4$ or N,

R$^1$ is C$_1$-C$_{30}$-alkyl, C$_2$-C$_{30}$-alkenyl, O—C$_1$-C$_{30}$-alkyl or O—C$_2$-C$_{30}$-alkenyl if X is C—R$^4$ or is CO—C$_1$-C$_{30}$-alkyl or CO—C$_2$-C$_{30}$-alkenyl if X is N, R$^2$ to R$^4$ are each hydrogen, C$_1$-C$_{30}$-alkyl or C$_2$-C$_{30}$-alkenyl, n is from 1 to 3, m is 0 or 1, p and q are each from 0 to 2 and Gly are mono- or disaccharides composed of aldopentoses, aldohexoses and/or ketohexoses.

The present invention furthermore relates to a process for the preparation of these glycosides, the corresponding diols as intermediates for this preparation process, the use of the bisglycosides I as surfactants or emulsifiers in detergents, cleaning agents and toiletries, and detergents, cleaning agents and toiletries containing the compounds I.

In the surfactant sector, nonionic surfactants based on renewable raw materials have become increasingly important over the past years. As a rule, such substances are readily biodegradable, have low toxicity and therefore possess good environmental compatibility.

An important group of such nonionic surfactants comprises alkylglycosides, as described in, for example, Tenside Surf Det. 26 (1989) 5, 318–324 (1), in which the long-chain hydrophobic alkyl radical is directly bonded to the hydrophilic carbohydrate moiety of the molecule by means of an acetal bond.

Although such products substantially meet expectations, some of their properties, such as the solubilizing power, are still unsatisfactory. It is also desirable for the surfactants partially o completely to act as complexing agents and/or builders in detergents and cleaning agents.

R. R. Schmidt in Angew. Chem. 98 (1986), 213–236 (2), describes the possible uses of O-glycosyl trichloroacetimidates and the use of the trifluoromethanesulfonate group as a further activating group in glycoside and oligosaccharide synthesis.

It is an object of the present invention to provide nonionic surfactants which are based on renewable raw materials and do not have the deficiencies described above.

We have found that this object is achieved by the bisglycosides I defined at the outset.

The linear or branched alkyl or alkenyl groups from which the radicals R$^1$ to R$^4$ are derived are of 1 to 30 or 2 to 30 carbon atoms, respectively. Groups of 6 to 22, in particular 10 to 18, carbon atoms give particularly good results. Optimum properties are obtained with a chain length of 14 to 16 carbon atoms, since this evidently corresponds to the optimum size ratio of hydrophobic to hydrophilic molecular moiety.

Examples of alkyl and alkenyl groups are methyl, ethyl, n-propyl, n-butyl, n-hexyl, n-octyl, 2-ethylhexyl, n-nonyl, isononyl, n-decyl, n-undecyl, n-qodecyl, n-tridecyl, tridecyl, isotridecyl, myristyl, cetyl, stearyl, eicosyl, vinyl, 1-propenyl, 2-propenyl, oleyl, linolyl and linolenyl.

If R$^1$ is bonded to a carbon atom, it is an alkyl or alkenyl group or an alkoxy or alkenyloxy group. If, on the other hand, R$^1$ is bonded to an N atom, it is an alkylcarbonyl or alkenylcarbonyl group.

R$^2$ to R$^4$ are preferably hydrogen or may be further alkyl or alkenyl groups.

n is in particular 1 but may furthermore be 2 or 3. m is 0 or 1. p and q independently of one another are each 0, 1 or 2, in particular both are 0.

The glycoside radical Gly is a mono- or disaccharide composed of conventional pentoses and/or ketoses. Building blocks of this type are aldopentoses, such as ribose, arabinose, xylose and lyxose, aldohexoses, such as allose, altrose, glucose, mannose, gulose, idose, galactose and talose, and ketohexoses-, such as fructose. Among these, mannose, glucose, galactose and fructose are preferred.

Disaccharides which may be used are in particular sucrose, lactose, maltose and cellobiose.

Depending on the preparation conditions for the bisglycosides I, small amounts of oligosaccharides having a degree of glycosidation of not more than 8 and of polysaccharides having a degree of glycosidation greater than 8 may be present as components in compounds I.

The naturally occurring carbohydrates of the D series are usually used, but members of the L series may also be employed.

The carbohydrate components are bonded to the remaining molecular moiety of I as a rule by an acetal bond at the anomeric carbon atom, i.e. at the 1-C atom, and both α and β anomers may be present.

Preferred bisglycosides are those of the general formula Ia $$\text{Gly—O—CHR}^2\text{—CHR}^1\text{—(CHR}^3)_m\text{—O—Gly} \quad \text{Ia}$$

where R$^1$ has the meanings stated for the case when X is C—R$^4$.

Further preferred bisglycosides are those of the general formula Ib $$\text{Gly—O—CHR}^2\text{—(CH}_2)_p\text{—NR}^1\text{—(CH}_2)_q\text{—CHR}^3\text{—O—Gly} \quad \text{Ib}$$

where R$^1$ has the meanings stated for the case when X is N.

The bisglycosides I are advantageously prepared by reacting (a) a diol of the general formula II $$\text{HO—CHR}^2\text{—(CH}_2)_p\text{(XR}^1)_n\text{—(CH}_2)_q\text{—(CHR}^3)_m\text{—OH} \quad \text{II}$$

with a protected glycosyl trihaloacetimidate of the general formula III $$\text{Gly'—O—}\overset{\overset{\displaystyle \text{NH}}{\displaystyle \|}}{\text{C}}\text{—CHal}_3 \quad \text{III}$$

where Hal is fluorine, chlorine or bromine and Gly' is a glycosyl radical of a mono- or disaccharide which is composed of aldopentoses, aldohexoses and/or ketohexoses and whose remaining hydroxyl groups carry conventional protective groups, or (b) a bistrifluoromethanesulfonate obtainable from a diol II and of the general formula IV

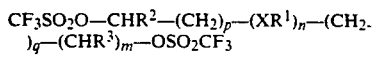    IV with a protected mono- or disaccharide of the general formula V

Gly'—OH    V and then removing the protective groups of the glycosyl radicals by a conventional method.

The synthesis methods which form the basis of the two procedures (a) and (b) and are conventionally used for these classes of substances are described in (2).

In the carbohydrate compounds III and V, all remaining hydroxyl groups apart from those which serve for bonding to the remaining molecular moiety of I and as a rule are attached to the anomeric carbon atom, i.e. to the 1-C atom, carry protective groups in order to prevent undesirable side reactions.

Examples of conventional protective groups for this purpose are the acetyl, benzyl or isopropylidene group, which, when the reaction is complete, can readily be eliminated again by a conventional method, for example by means of catalytic amounts of a sodium alcoholate or by means of protic acids, such as acetic acid.

In the trihaloacetimidate method (a), the diols II are reacted with the acetimidates III, usually in the presence of a catalytic amount of a protic acid or of a Lewis acid. Lewis acids, such as tin tetrachloride, titanium tetrachloride and especially boron trifluoride adducts, e.g. boron trifluoride etherate, are preferably used for this purpose. Among the acetimidates III, the trichloroacetimidates are most advantageously used.

In method (a), the reaction is carried out as a rule in an anhydrous inert solvent, such as n-pentane, n-hexane, cyclohexane, toluene, chloroform, dichloromethane, tetrahydrofuran or diethyl ether, or in a mixture of such solvents at room temperature or slightly elevated temperatures up to about 50° C. and at atmospheric pressure. The reactions are generally complete after from 1 to 5 hours. Chromatographic methods are most suitable for any purification of the product.

In the trifluoromethanesulfonate method (b), the bistrifluoromethanesulfonates IV obtainable from the diols II, for example by reaction with trifluoromethanesulfonic anhydride, are reacted with the carbohydrates V, as a rule in the presence of a strong base, such as an alkali metal alcoholate or an alkali metal hydride. The reaction is usually carried out in an anhydrous inert solvent as in (a), at room temperature or slightly elevated temperatures up to about 80° C. and at atmospheric pressure. It is advisable to use a protective gas, such as nitrogen or argon. Chromatographic methods are most suitable for any purification of the product.

The present invention furthermore relates to diols of the general formula II

HO—CHR$^2$—(CH$_2$)$_p$—(XR$^1$)$_n$—(CH$_2$)$_q$—(CHR$^3$)$_m$—OH    II as intermediates for the preparation of the bisglycosides I.

The bisglycosides I are used as surfactants, mainly as nonionic surfactants or emulsifiers, in detergents and cleaning agents, for example for industrial and household cleaning processes, such as the washing of textiles, or for cleaning processes in the food sector, such as the cleaning of beverage bottles. They are also used as emulsifier in toiletries, such as skin creams, lotions, gels, skin oils or hair shampoos.

In detergents and cleaning agents, the bisglycosides I also act as complexing agents and builders, this activity being due to the chelating effect of the two carbohydrate units. As a result of the interaction with the hydroxyl groups of the carbohydrate moieties, metal ions, such as calcium, magnesium and iron ions, are complexed, reinforcing the washing action.

The present invention also relates to detergents, cleaning agents and toiletries which contain from 1 to 50, preferably from 5 to 30, % by weight of a bisglycoside I or of a mixture of such bisglycosides. The conventional components and composition of detergents and cleaning agents and of toiletries are familiar to the skilled worker and therefore need not be described further here.

The novel bisglycosides I result in a low surface tension of from about 30 to about 50 mN/m and especially a very low critical micelle concentration (CMC) of from about 1 to about 0.001 mmol/l. The low CMC values are an expression of the excellent solubilizing power of the compounds I. Hence, substantially lower concentrations of the novel compounds I, compared with conventional alkylglycosides, are required in detergent, cleaning agent and toiletry formulations.

The readily biodegradable bisglycosides I also have the advantage that they additionally act as complexing agents and builders in detergents and cleaning agents and can thus partially or completely replace conventional poorly biodegradable complexing agents and builders, enabling environmental pollution to be reduced.

PREPARATION EXAMPLES

Example 1

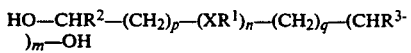

2.05 g (4.18 mmol) of 2,3,4,6-tetra-O-acetyl-α-D-glucopyranosyl trichloroacetimidate and 0.43 g (2.0 mmol) of 2-hydroxymethyl-1-dodecanol were dissolved in 20 ml of a mixture of equal amounts by volume of anhydrous n-hexane and anhydrous dichloromethane. 2.0 g of a roughly 1.5% strength by weight solution of boron trifluoride etherate in diethyl ether (corresponding to 0.2 mmol of BF$_3$.Et$_2$O) were slowly added dropwise in the absence of moisture.

After stirring had been carried out for 2.5 hours at room temperature, 0.3 g of sodium bicarbonate and 20 ml of dichloromethane were added. The mixture was filtered, the solvent was distilled off and the resulting crude product was purified by flash chromatography using 7:3 toluene/ethyl acetate, after which the product was dissolved in 60 ml of anhydrous methanol and the acetyl protective groups were eliminated by stirring for 5 hours with 0.5 ml of a 0.1 molar sodium methoxide solution in methanol at room temperature.

After treatment with acidic ion exchanger material, the solution was evaporated down under reduced pressure from a water pump and the end product was purified by flash chromatography using 5:3 dichloromethane/methanol. The title compound was obtained in a yield of 52% and had a melting point of 146°–146.5° C. and a specific rotation $[\alpha]_D^{20}$ of −24.7°.

Example 2

2-(α-D-glucopyranosyloxymethyl)-tetradecyl-1-β-D-glucopyranoside

The title compound was prepared in a yield of 53% similarly to Example 1, starting from 2-hydroxymethyl-1-tetradecanol. It had a melting point of 181.1°–181.6° C. and a specific rotation $[\alpha]_D^{20}$ of $-8.5°$.

Example 3

2-(β-D-glucopyranosyloxymethyl)-hexadecyl-1-β-D-glucopyranoside

The title compound was prepared in a yield of 69% similarly to Example 1, starting from 2-hydroxymethyl-1-hexadecanol. It had a melting point of 154.1°–154.6° C. and a specific rotation $[\alpha]_D^{20}$ of $-18.2°$.

Example 4

2-(β-D-glucopyranosyloxymethyl)-octadecyl-1-β-D-glucopyranoside

The title compound was prepared in a yield of 43% similarly to Example 1, starting from 2-hydroxymethyl-1-octadecanol. It had a melting point of 214.1°–214.7° C. and a specific rotation $[\alpha]_D^{20}$ of $-9.7°$.

Example 5

2-Decyloxy-3-(β-glucopyranosyloxy)-propyl-1-β-D-glucopyranoside

The title compound was prepared in a yield of 62% similarly to Example 1, starting from 2-decyloxy-1,3-propanediol. It had a melting point of 164.5°–164.8° C. and a specific rotation $[\alpha]_D^{20}$ of $-12.9°$.

Example 6

2-Decyloxy-1,3-di-(β-D-mannofuranosyloxy)-propane 3.90 g (15.0 mmol) of 2,3:5,6-di-O-isopropylidenemannofuranose were dissolved in 100 ml of anhydrous toluene under nitrogen as protective gas, and 400 mg of sodium hydride were added. After evolution of hydrogen had ceased, the mixture was heated to 50° C. 3.72 g (7.5 mmol) of 2-decyloxy-1,3-di-(trifluoromethanesulfonyloxy)-propane were slowly added dropwise.

After the reaction had ended, excess sodium hydride was decomposed with methanol while cooling, 200 ml of ethyl acetate were added to the reaction mixture and the latter was washed with saturated NaCl solution and water. After the solution had been dried over $MgSO_4$ and evaporated down under reduced pressure from a water pump, the crude product was purified by flash chromatography using 5:3 petroleum ether/ethyl acetate.

The isopropylidene protective groups were removed by stirring the resulting product for 5 days in 120 ml of 70% strength by weight acetic acid at room temperature. After acetic acid and water had been distilled off under reduced pressure from a water pump, the end product was purified by flash chromatography using 14:6:1 dichloromethane/methanol/water. The title compound was obtained in a yield of 55%.

Example 7

2-Dodecyloxy-1,3-di-(β-D-mannofuranosyloxy)-propane

The title compound was prepared in a yield of 58% similarly to Example 6, starting with 2-dodecyloxy-1,3-di-(trifluoromethanesulfonyloxy)-propane.

Example 8

2-Hexadecyloxy-1,3-di-(β-D-mannofuranosyloxy)-propane

The title compound was prepared in a yield of 59% similarly to Example 6, starting with 2-hexadecyloxy-1,3-di-(trifluoromethanesulfonyloxy)-propane.

Performance Characteristics

The bisglycosides from Examples 1 to 5 (X=CH, $R^2=R^3=H$), n=m=1, p=q=0 and Gly=glycosyl) were investigated to determine their critical micelle concentration (CMC) and their surface tension. The corresponding values for decyl- and dodecyl-β-D-glucoside from Table 2 of reference (1) were used as Comparative Examples.

The CMC values were determined at 20° C. by the conventional method.

The surface tension was measured according to DIN 53,914. The force, in mN/m, required to pull a horizontally suspended ring or bracket out of the liquid surface was measured.

The Table below shows the results of the measurements:

| Bisglycoside | $R^1$ | CMC [mmol/l] | Surface tension [mN/m] |
|---|---|---|---|
| of Example 1 | n-Decyl | 0.594 | 42.3 |
| of Example 2 | n-Dodecyl | 0.065 | 38.9 |
| of Example 3 | n-Tetradecyl | 0.0026 | 38.5 |
| of Example 4 | n-Hexadecyl | 0.0619 | 44.1 |
| of Example 5 | n-Decyloxy | 0.472 | 46.8 |
| For comparison: | | | |
| Decyl-β-D-glucoside | | 1.9 | 30.5 |
| Dodecyl-β-D-glucoside | | 0.08 | 36 |

We claim:

1. A bisglycoside of the formula I

Gly—O—$CHR^2$—$(CH_2)_p$—$(XR^1)_n$—$(CH_2)_q$—$(CHR^3)_m$—O—Gly  I

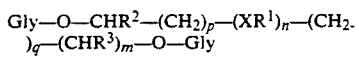

where

X is C—$R^4$ or N, $R^1$ is $C_1$-$C_{30}$-alkyl, $C_2$-$C_{30}$-alkenyl, O—$C_1$-$C_{30}$-alkyl or O—$C_2$-$C_{30}$-alkenyl when X is C—$R^4$ or is CO—$C_1$-$C_{30}$-alkyl or CO—$C_2$-$C_{30}$-alkenyl when X is N, $R^2$ to $R^4$ are each hydrogen, $C_1$-$C_{30}$-alkyl or $C_2$-$C_{30}$-alkenyl, n is from 1 to 3, m is 0 or 1, p and q are each from 0 to 2 and Gly is a mono- or disaccharide selected from the group consisting of an aldopentose, an aldohexose, a ketohexose, or a combination thereof.

2. A bisglycoside I as claimed in claim 1, in which the alkyl or alkenyl groups from which the radicals $R^1$ to $R^4$ are derived are each of 6 to 22 carbon atoms.

3. A bisglycoside of the formula Ia as claimed in claim 1

$$Gly-O-CHR^2-CHR^1-(CHR^3)_m-O-Gly \qquad Ia$$

where $R^1$ has the meanings stated for the case when X is $C-R^4$.

4. A bisglycoside of the formula Ib as claimed in claim 1

$$Gly-O-CHR^2-(CH_2)_p-NR^1-(CH_2)_q-CHR^3-O-Gly \qquad Ib$$

where $R^1$ has the meanings stated for the case when X is N.

* * * * *